US00PP26735P3

(12) United States Plant Patent
Labonte et al.

(10) Patent No.: US PP26,735 P3
(45) Date of Patent: May 17, 2016

(54) SWEETPOTATO PLANT NAMED 'LA06-52'

(50) Latin Name: *Ipomoea batatas*
Varietal Denomination: LA06-52

(71) Applicant: Board of Supervisors of Louisiana State University and Agricultural and Mechanical College Through The LSU AgCenter, Baton Rouge, LA (US)

(72) Inventors: Don R. Labonte, Baton Rouge, LA (US); Arthur Q. Villordon, Monroe, LA (US); Tara P. Smith, Chase, LA (US); Christopher A. Clark, Baton Rouge, LA (US)

(73) Assignee: Board of Supervisors of Louisiana State University and Agricultural and Mechanical College Through The LSU AgCenter, Baton Rouge, LA (US)

( * ) Notice: Subject to any disclaimer, the term of this patent is extended or adjusted under 35 U.S.C. 154(b) by 186 days.

(21) Appl. No.: 13/999,592

(22) Filed: Mar. 11, 2014

(65) Prior Publication Data

US 2015/0264851 P1 Sep. 17, 2015

(51) Int. Cl.
*A01H 5/06* (2006.01)

(52) U.S. Cl.
USPC ..... Plt./258

(58) Field of Classification Search
USPC ..... Plt./258
See application file for complete search history.

*Primary Examiner* — Susan McCormick Ewoldt
*Assistant Examiner* — Karen Redden
(74) *Attorney, Agent, or Firm* — James C. Carver

(57) ABSTRACT

A new variety of sweetpotato identified as 'LA06-52' is disclosed having disease resistance to *Fusarium* wilt, *Rhizopus* soft rot (intermediate), southern root-knot nematode, and *Streptomyces* soil rot, an orange flesh, copper skin and high yield characteristics.

3 Drawing Sheets

Latin name: *Ipomoea batatas.*

Varietal denomination: 'LA06-52'.

This invention pertains to a new and distinct variety of sweetpotato.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

Genus and Species Name

This new and distinct sweetpotato variety, *Ipomoea batatas* (L.) Lam., demonstrates superior disease resistance to southern root-knot nematode and exhibits an orange flesh. It also demonstrates a copper skin in comparison to light to medium rose skinned 'Beauregard'.

Variety Denomination

This new and distinct sweetpotato variety is identified as 'LA06-52', and is characterized by an orange flesh, high yield, consistent shape, and a copper skin.

BRIEF DESCRIPTION OF THE DRAWINGS

The file of this patent contains at least one photograph executed in color. Copies of this patent or patent application with color drawing(s) will be provided by the Patent and Trademark Office upon request and payment of the necessary fee.

DETAILED BOTANICAL DESCRIPTION

This new variety of sweetpotato, named 'LA06-52', resulted from an open pollinated cross performed in 2005 to the female parent '82-529' (not patented). The male parent was unknown. Four patented male parents ('L96-117' patented U.S. Plant Pat. No. 15,038 P2; 'Bienville' patented U.S. Plant Pat. No. 15,380 P3; 'Evangeline' patented U.S. Plant Pat. No. 19,710 P3, and 'Murasaki-29' patented U.S. Plant Pat. No. 19,955 P2) were among the potential pollen sources in the crossing nursery. 'LA06-52' was developed to provide a variety with characteristics similar to 'Beauregard' (unpatented), but with a copper skin and southern root-knot nematode resistance. None of the potential patented pollen sources have a copper skin.

Plants of 'LA06-52' and 'Beauregard' can be differentiated. 'LA06-52' immature leaves are dark purple [10 P (purple) (2/4)] which extend from the apex to leaves on the $7^{th}$ node. 'Beauregard' infrequently has dark purple immature leaves and never extending to the $7^{th}$ node. Color terminology used herein is in accordance with the Munsell® Book of Color (Munsell Color, GretagMacbeth LLC, 617 Little Britain Road, New Windsor, N.Y. 12553-6148, published August 2003). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'LA06-52'.

'LA06-52' roots were stored during the winter at Chase, La. 'LA06-52' was planted the following spring, resulting in approximately 8-10 sprouts per root. Cuttings from the sprouts were transplanted successfully for asexual reproduction. Asexual propagation of the new cultivar by cuttings has shown that the unique features of this new sweetpotato were stable and that the plant reproduced true to type in successive generations of asexual propagation. Plants described herein were 90 days in age from planting in full sun field plantings.

Figure 1:
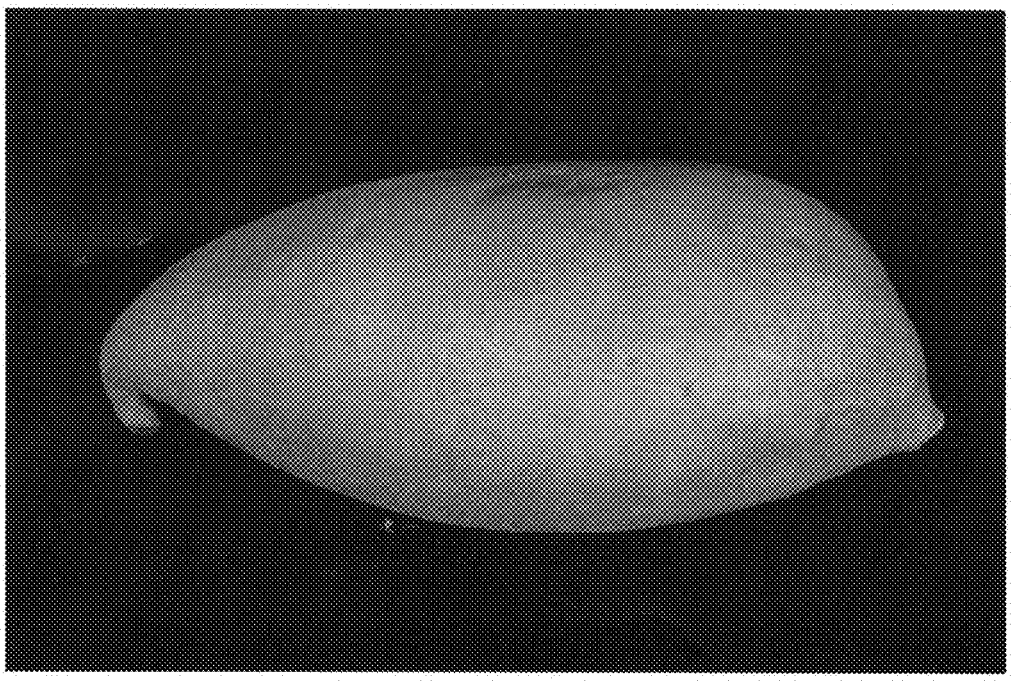
FIG. 1 is a color photograph of the fleshy root form of the novel variety of sweetpotato identified as 'LA06-52'.
Figure 2:
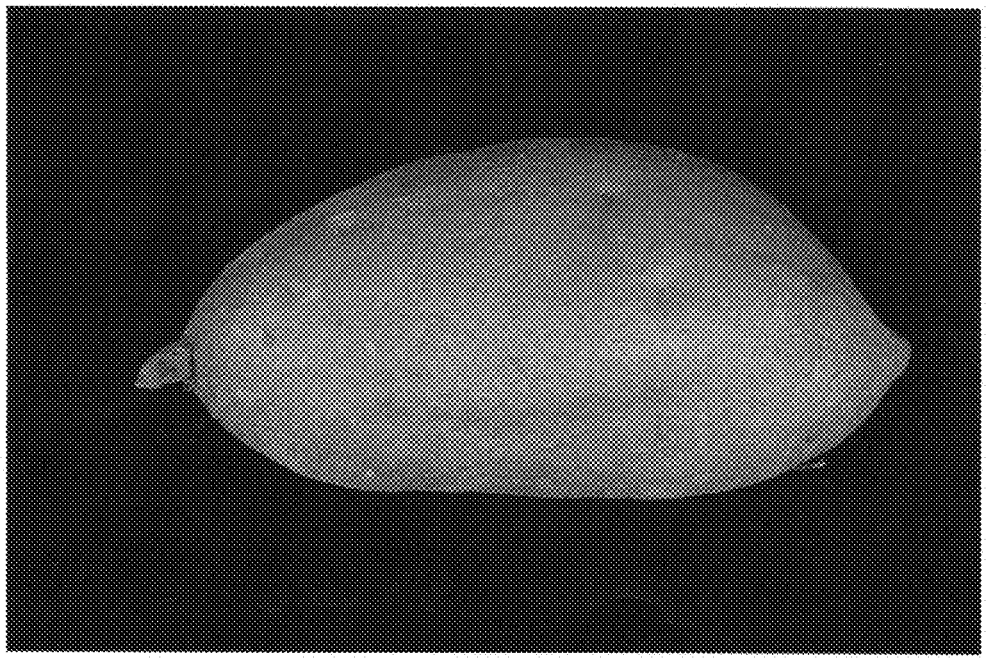
FIG. 2 is a color photograph of the fleshy root form of the sweetpotato variety identified as 'Beauregard'.

FIG. 1 depicts the fleshy root form of the 'LA06-52' sweetpotato. The skin is a light copper and differs from the light to medium rose 'Beauregard', both at harvest and after several months of storage as shown in Table 1. Munsell® Book of Color values for skin and flesh for both 'LA06-52' and 'Beauregard' storage roots after 6 months of storage are shown in Table 1. The 'Beauregard' sweetpotato is depicted in FIG. 2. The skin for both 'LA06-52' and 'Beauregard' was smooth. 'LA06-52' storage roots were elliptical without lobing, and tend to be shorter than 'Beauregard' in varied soil types. Nodal eyes are not present in sweetpotato as they are a *Solanum* potato; lateral root scars are seldom present. 'LA06-52' has a smooth skin with few indentations. The 'LA06-52' cortex was 5 mm in depth and the color similar throughout. The flesh of 'LA06-52' is orange in comparison to the lighter flesh of 'Beauregard'.

TABLE 1

| Variable | Variety | Color |
|---|---|---|
| Skin | 'LA06-52' | 5 Y (yellow) R (red) 7/4 |
| | 'Beauregard' | 10 R (red) 6/6 |
| Flesh | 'LA06-52' | 5 Y (yellow) R (red) 7/10 |
| | 'Beauregard' | 2.5 Y (yellow) R (red) 7/8 |

Figure 3:
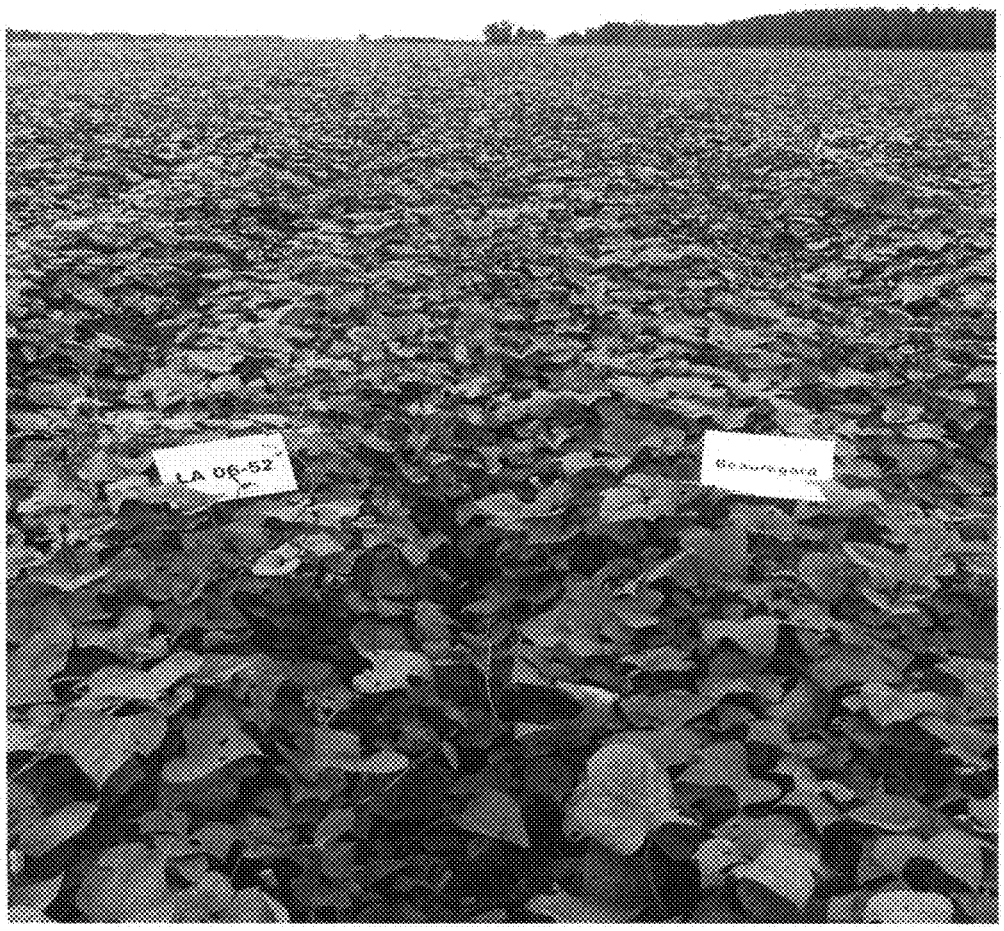
FIG. 3 is a color photograph of the canopy biomasses of the variety of sweetpotato identified as 'Beauregard' (shown on the right side of the photograph) and the novel variety identified as 'LA06-52' (shown on the left side of the photograph).

FIG. 3 depicts the canopy biomass of both 'LA06-52' sweetpotatoes and 'Beauregard' sweetpotatoes. 'LA06-52' has round, green-stemmed vines which change [2.5 G (green) Y (yellow) (5/6)] from the apex to purple [2.5 R (red) P (purple) 2/8] 30-40 cm from the apex and extends to the crown of the roots. The first 4 cm of the stem from the apex is weakly pubescent before becoming glabrous. The 'LA06-52' canopy biomass is greater than 'Beauregard'. The 'LA06-52' canopy architecture was 31 cm in height from the soil surface and 121 cm in a radial spread and slightly less than 'Beauregard' (182 cm). For 'LA06-52', three main vines arose from the main stem near the soil surface. The stem giving rise to these vines was 1.0-1.5 cm in diameter; the 3 lateral vines were 180 cm in length with diameters of about 0.5 cm at 65 cm from the base and diameters of about 0.6 cm at the first internode of the first fully developed leaf from the apex. Four to six lateral branches arose from each of the main vines. At the first internode from the apex, the internode length was about 5.5 cm between the first and second fully developed leaves. Internode lengths for other sections of the vine averaged about 7 cm. Unfolded immature leaves were dark purple [10 P (purple) (2/6)] for the upper and lower surface, which change gradually over 7 nodes from the apex to a dark green upper surface [7.5 G (green) Y (yellow) (3/4)] to a dark green lower surface [7.5 G (green) Y (yellow) (4/2)]. Mature leaves at five nodes from the apex had an acute apex and mostly a cordate base and a smooth leaf margin. Mature leaves were about 9.7 cm long and 10 cm wide. Leaves were glabrous, without undulations, and pliable. The abaxial surface has prominent raised veins; abaxial and adaxial veins are in pinnate venation pattern, and were slightly purple [7.5 R (red) P (purple) (4/4)]. The petiole was green [7.5 (3 (green) Y (yellow) (3/4)]. A purple [7.5 R (red) P (purple) (4/4)] marking was at the base of the leaf junction with the petiole. The round, glabrous petiole was 8.5 cm long at five nodes from the apex, and 3 mm in diameter at 5 cm from the leaf junction. The dormant nodal meristem was green [2.5 G (green) Y (yellow) (5/6)].

A typical inflorescence of 'LA06-52' displayed two clusters of six flowers per peduncle. Peduncles were green [2.5 G (green) Y (yellow) (5/8)], about 8-12 cm long, and about 3 mm in diameter. Individual flowers were about 3.6 cm long from the base of the calyx, and the corolla was 3 to 3.5 cm wide at the opening. The fused flower petals formed a pentagonal pattern with smooth edges. The inner throat of the corolla appeared purple [7.5 P (purple) (4/6)]. The inner and outer limbs of the corolla (corollas outermost area, distal from the calyx) were light purple [10 P (purple) (7/4)]. The five sepals comprising the calyx were elliptic with a cordate apex and appeared to be green [2.5 G (green) Y (yellow) (5/6)]; three of these sepals were about 11 mm long and 4 mm wide. Two other sepals (interspersed) were about 6 mm long and 2 mm wide. Sepal margins were smooth. Stigmata were about 1.7 cm long and appeared purple [7.5 R (red) P (purple) (8/6)] at the base before fading. Five stamens were inferior to the stigmata. A slight fragrance was present.

EXAMPLE 1

Tests Conducted

'LA06-52' did not appear to show any novel insect resistance.

To confirm that 'LA06-52' was a new variety, controlled tests (e.g., pathogen responses and yield) were conducted in Baton Rouge, La. 'Beauregard' was selected for comparison because of its importance in commercial United States orange flesh sweetpotato acreage. Diseases that commonly affect the growth of sweetpotatoes were selected to test for pathogen responses in both varieties. 'LA06-52' was resistant for *Streptomyces* soil rot caused by *Streptomyces ipomoeae* (Person & W. J. Martin) Waksman & Henrici, while 'Beauregard' was intermediate to resistant. 'LA06-52' and 'Beauregard' were resistant to *Fusarium* wilt or stem rot caused by *Fusarium oxysporum* Schlect. f. sp. *batatas* (Wollenw.) Snyd. & Hans.

Nematode reproduction was measured in greenhouse tests. 'LA06-52' was highly resistant while 'Beauregard' was susceptible to southern root-knot nematode, *Meloidogyne incognita* (Kofoid & White 1919) Chitwood 1949. 'LA06-52' and 'Beauregard' were intermediate to *Rhizopus* soft rot caused by *Rhizopus stolonifer* (Ehr. ex. Fr.) Lind as measured by postharvest inoculation of storage roots. 'LA06-52' was very susceptible to bacterial root rot caused by *Dickeya dadantii* Samson et al, while 'Beauregard' was susceptible as measured by postharvest inoculation of storage roots.

To determine yield production, complete-block trials using four replications of 'LA06-52' and 'Beauregard' each were conducted in 2007, 2011, 2012, and 2013 in areas of Louisiana, Arkansas, Missouri, and California likely to produce 'LA06-52'. 'LA06-52' and 'Beauregard' sweetpotato plants were transplanted in randomized complete-block trials at 31 cm spacings. Each block/plot was fertilized with approximately 250 pounds per acre of a mixed fertilizer comprising 13% N, 13% $P_2O_5$, and 13% $K_2O$. 'LA06-52' was compared to 'Beauregard' at transplanting dates beginning in May-July. Average yields were measured for the following grades of roots: U.S. #1 (51-89 mm in diameter, 76-229 mm long); Canner (25-51 mm in diameter, 51-178 mm long), and Jumbo (larger than U.S. #1 in diameter, length or both, and without objectionable defects). A typical marketable root of 'LA06-52' was 180-190 mm long, 70-80 mm in diameter, with mostly elliptic shape. The base or distal end tended to be similar to the apex (proximal end). U.S. #1 roots typically weighed 150-190 g.

A mid-season transplanting date trial was conducted at Sikeston, Mo. in 2012. '06-52' and 'Beauregard' were transplanted on Jun. 6, 2012, and harvested on Sep. 26, 2012 (112 days after planting). Average yields, measured as Metric Tons per Hectare ($MT \cdot ha^{-1}$), are shown in Table 2.

TABLE 2

| Selection | US#1† | Canners† | Jumbos† | TMY‡† |
|---|---|---|---|---|
| 'LA06-52' | 41.8a | 8.1a | 25.4a | 75.4a |
| 'Beauregard' | 22.4b | 9.1a | 30.5a | 62.0a |

†Average yields in $MT \cdot ha^{-1}$ of varieties followed by a common letter do not differ significantly ($P < 0.05$) according to Duncan's Multiple Range Test
TMY‡ = total marketable yield An early season transplanting date trial was also conducted at Grand Prairie, La. on May 31, 2012, and harvested on Oct. 4, 2012 (126 days after planting). Average yields ($MT \cdot ha^{-1}$) by grade of 'LA06-52' and 'Beauregard' are shown in Table 3.

TABLE 3

| Selection | US#1† | Canners† | Jumbos† | TMY‡† |
|---|---|---|---|---|
| 'LA06-52' | 14.9a | 10.1a | 0.5a | 25.4a |
| 'Beauregard' | 21.3a | 8.9a | 1.2b | 31.4b |

†Average yields in $MT \cdot ha^{-1}$ of varieties followed by a common letter do not differ significantly ($P < 0.05$) according to Duncan's Multiple Range Test
TMY‡ = total marketable yield An early season transplanting date trial was also conducted at Grand Prairie, La. on Jun. 26, 2013, and harvested on Oct. 22, 2013 (119 days after planting). Average yields ($MT \cdot ha^{-1}$) by grade of 'LA06-52' and 'Beauregard' are shown in Table 4.

TABLE 4

| Selection | US#1† | Canners† | Jumbos† | TMY‡† |
|---|---|---|---|---|
| 'LA06-52' | 25.6a | 7.1a | 11.3a | 44.0a |
| 'Beauregard' | 9.64a | 9.1a | 12.2b | 30.9a |

†Average yields in $MT \cdot ha^{-1}$ of varieties followed by a common letter do not differ significantly ($P < 0.05$) according to Duncan's Multiple Range Test
TMY‡ = total marketable yield A mid to late season transplanting date trial was also conducted at Montrose, Ak. on Jun. 13, 2012, and harvested on Oct. 19, 2012 (118 days after planting). Average yields ($MT \cdot ha^{-1}$) by grade of 'LA06-52' and 'Beauregard' are shown in Table 5.

TABLE 5

| Selection | US#1† | Canners† | Jumbos† | TMY‡† |
|---|---|---|---|---|
| 'LA06-52' | 20.1 a | 14.8a | 1.0a | 35.9a |
| 'Beauregard' | 17.1a | 25.0a | 3.8a | 45.9a |

†Average yields in $MT \cdot ha^{-1}$ of varieties followed by a common letter do not differ significantly ($P < 0.05$) according to Duncan's Multiple Range Test
TMY‡ = total marketable yield A mid to late-season transplanting date trial was also conducted at Sikeston, Mo. on Jun. 21, 2013, and harvested on Oct. 28, 2013 (130 days after planting). Average yields ($MT \cdot ha^{-1}$) by grade of 'LA06-52' and 'Beauregard' are shown in Table 6.

TABLE 6

| Selection | US#1† | Canners† | Jumbos† | TMY‡† |
|---|---|---|---|---|
| 'LA06-52' | 34.4a | 7.2a | 5.2a | 46.8a |
| 'Beauregard' | 21.6a | 4.8a | 4.4a | 30.8a |

†Average yields in $MT \cdot ha^{-1}$ of varieties followed by a common letter do not differ significantly ($P < 0.05$) according to Duncan's Multiple Range Test
TMY‡ = total marketable yield A late-season transplanting date trial was also conducted at Chase, La. on Jul. 2, 2007, and harvested on Nov. 11, 2007 (132 days after planting). Average yields ($MT \cdot ha^{-1}$) by grade of 'LA06-52' and 'Beauregard' are shown in Table 7.

TABLE 7

| Selection | US#1† | Canners† | Jumbos† | TMY‡† |
|---|---|---|---|---|
| 'LA06-52' | 23.1a | 9.1a | 6.3a | 38.6a |
| 'Beauregard' | 24.4a | 10.1a | 6.3a | 37.5a |

†Average yields in $MT \cdot ha^{-1}$ of varieties followed by a common letter do not differ significantly ($P < 0.05$) according to Duncan's Multiple Range Test.
TMY‡ = total marketable yield A late-season transplanting date trial was also conducted at Livingston, Calif. on Jun. 2, 2011, and harvested on Oct. 25, 2011 (145 days after planting). This represents a later planting date compared to other production regions. Average yields ($MT \cdot ha^{-1}$) by grade of 'LA06-52' and 'Beauregard' are shown in Table 8.

TABLE 8

| Selection | US#1† | Canners† | Jumbos† | TMY‡† |
|---|---|---|---|---|
| 'LA06-52' | 8.4b | 12.1a | 4.8b | 25.4b |
| 'Beauregard' | 14.1a | 12.3a | 13.0a | 39.4a |

†Average yields in $MT \cdot ha^{-1}$ of varieties followed by a common letter do not differ significantly ($P < 0.05$) according to Duncan's Multiple Range Test.
TMY‡ = total marketable yield As shown in Tables 2-8, 'LA06-52' produced yields comparable to, and exceeding 'Beauregard' in regional trials at various planting dates. Yield in comparison to 'Beauregard' in heavier silt loam soils (Tables 3, 4, and 7) were similar to outcomes in lighter, sandy loam soils (Tables 2, 5, 6 and 8). The Livingston, Calif. plot was lower in yield than 'Beauregard' for the important U.S. #1 grade; however, other plots in California have demonstrated strong yields (19-30 $MT \cdot ha^{-1}$). There is a tendency for higher yield in early and middle season plots in comparison to late season plantings (Tables 7 and 8). Yield declines are within norms in poor environments. 'LA06-52' had harvestable roots approximately 120 days after planting, which is typical development time for sweetpotatoes and comparable to 'Beauregard'. The yield of Jumbo grade is indicative of earliness and 'LA06-52' was similar to the jumbo yield of 'Beauregard', statistically; however, rank changed from plot to plot. Yield of 'LA06-52' for U.S. #1 grade was significantly higher in one plot in 2012 and lower in one in 2011 in comparison to 'Beauregard'. In total, this data reflects consistent high yield characteristics for 'LA05-62'.

Sugar profiles for baked 'LA06-52' and 'Beauregard' are shown in Table 9. For this 2012 test, roots were stored for three months after which they were baked at 190° C. for approximately 2.0 h. Sucrose content in baked 'LA06-52' was similar to that found in baked 'Beauregard'; maltose content was lower in comparison to 'Beauregard'. Total sugar content was similar for 'LA06-52' and 'Beauregard' on a sucrose equivalency basis. High fructose content in 'LA06-52' compensated for lower maltose content. Dry matter is slightly less for 'LA06-52' (20.5%) in comparison to 'Beauregard' (21.3%). These results demonstrate a similar level of sweetness and moistness for 'LA06-52' and 'Beauregard'.

TABLE 9

| Selection | Fructose‡ | Glucose‡ | Sucrose‡ | Maltose‡ | Total sugars†‡ |
|---|---|---|---|---|---|
| 'LA06-52' | 1.79 | 2.36 | 2.41 | 2.16 | 8.72 |
| 'Beauregard' | 0.96 | 1.20 | 2.30 | 4.89 | 9.35 |

†Total sugars = fructose + glucose + maltose + sucrose.
‡$mg \cdot g^{-1}$ fresh weight basis 'LA06-52' should be a valuable commercial sweetpotato variety. 'LA06-52' produced plants (sprouts) comparable to commercial varieties lay California; however, plant production is below that of 'Beauregard' in Louisiana. Days to harvest for 'LA06-52' were similar to 'Beauregard'. 'L06-52' exhibited different sugar profiles in comparison to 'Beauregard'; however, sucrose equivalency was similar.

We claim:

1. A new and distinct variety of *Ipomoea batatas* plant named 'LA06-52' as described and illustrated in the specification herein.

* * * * *